United States Patent [19]
Russell-Jones et al.

[11] Patent Number: 5,589,463
[45] Date of Patent: Dec. 31, 1996

[54] ORAL DELIVERY OF BIOLOGICALLY ACTIVE SUBSTANCES BOUND TO VITAMIN B12

[75] Inventors: Gregory J. Russell-Jones, Willoughby; Peter Howe, West Pennant Hills; Henry J. de Aizpurua, Bexley; Geoffery L. Burge, Thornleigh, all of Australia

[73] Assignee: Biotechnology Autralia Pty., Ltd., Roseville, Australia

[21] Appl. No.: 479,635

[22] Filed: Jun. 7, 1995

Related U.S. Application Data

[62] Division of Ser. No. 61,343, May 17, 1993, Pat. No. 5,428,023, which is a continuation of Ser. No. 759,697, Sep. 9, 1991, abandoned, which is a continuation of Ser. No. 600,137, Oct. 19, 1990, abandoned, which is a continuation of Ser. No. 84,821, Jun. 9, 1987, abandoned.

[30] Foreign Application Priority Data

Oct. 10, 1985 [AU] Australia .................... PH2838

[51] Int. Cl.⁶ .................. A61K 31/715; A61K 39/385; C07H 23/00
[52] U.S. Cl. .................. 514/21; 424/194.1; 514/12; 514/52; 530/405; 536/26.4; 536/26.41; 536/26.44
[58] Field of Search ............... 422/61; 435/86; 424/85.4, 94.1, 193.1, 194.1; 514/2, 4, 6, 12, 15, 21, 52, 80, 800; 536/26.4, 26.41, 26.44; 530/303, 304, 306, 307, 313, 315, 345, 362, 351, 391.7, 391.9, 398, 399, 405, 409

[56] References Cited

U.S. PATENT DOCUMENTS

| | | | |
|---|---|---|---|
| 2,372,066 | 3/1945 | Fell | 530/386 |
| 3,042,588 | 7/1962 | Heathcote | 530/345 |
| 3,459,855 | 8/1969 | Thuiller | 514/52 |
| 3,920,631 | 11/1975 | Molteni et al. | 536/25 |
| 3,981,863 | 9/1976 | Niswender et al. | 536/25 |
| 4,062,936 | 12/1977 | Ogawa et al. | 436/823 |
| 4,133,951 | 1/1979 | Charlton et al. | 536/25 |
| 4,209,614 | 6/1980 | Bernstein et al. | 536/25 |
| 4,235,866 | 11/1980 | Thoma | 424/1 |
| 4,360,358 | 11/1982 | Sharma | 422/61 |
| 4,364,939 | 12/1982 | Autissier et al. | 536/25 |
| 4,377,570 | 3/1983 | Ourette et al. | 514/8 |
| 4,452,775 | 6/1984 | Kent | 424/19 |
| 4,454,125 | 6/1984 | Demopoulos | 514/52 |
| 4,465,775 | 8/1984 | Houts | 536/25 |
| 4,508,832 | 4/1985 | Carter et al. | 436/517 |
| 4,746,508 | 5/1988 | Carey et al. | 424/88 |
| 4,751,285 | 6/1988 | Toohey | 530/331 |
| 5,428,023 | 6/1995 | Russell-Jones et al. | 514/21 |

FOREIGN PATENT DOCUMENTS

| | | |
|---|---|---|
| 79929/87 | 4/1988 | Australia . |
| 0036277 | 9/1981 | European Pat. Off. . |
| 2111895 | 9/1972 | France . |
| 2546474 | 4/1977 | Germany . |
| 0467277 | 2/1969 | Switzerland . |
| 1123853 | 8/1968 | United Kingdom . |
| 1152461 | 5/1969 | United Kingdom . |
| 1345327 | 1/1974 | United Kingdom . |
| 88/00474 | 1/1988 | WIPO . |
| 88/07365 | 10/1988 | WIPO . |
| 89/08449 | 9/1989 | WIPO . |

OTHER PUBLICATIONS

Albert, A., "Heterocyclic Chemistry", p. 143 (1959).
Laurence, G. S., *Trans. Faraday Soc.* vol. 52, pp. 236–242 (1955).
Sillen L. G. and A. E. Martell, "Stability Constants of Metal Ion Complexes", *Chem. Soc. Special Publication No. 17*, pp. iii, v, vii, 1 and 357 (1964).
Wallenfels, K. and C. Streffer, *Biochem. Zeit,* vol. 346, pp. 119–132 (1966).
Hamada, S., *J. Chem. Soc. Japan* vol. 82, p. 1327 (1961).
Grant, ed., *Hackh's Chemical Dictionary*, 4th Edition, McGraw–Hill Book Co., pp. 192, 715 (1969).
Bloom et al., *Mount Sinai J. Medicine*, vol. 48, No. 5, pp. 397–403 (1981).
Kinter, W. B. et al., "Autoradiographic Study of Sugar and Amino Acid Absorption by Everted Sacs of Hamster Intestine", *J. Cell Biol.*, vol. 25, pp. 19–39 (1965).
Mathews, D. M. et al., "Progress in Gastroenterology: Peptide Absorption", *Gastroenterol,* vol. 71, pp. 151–161 (1976).
Alpers, D. H., "Uptake and Fate of Absorbed Amino Acids and Peptides in the Mammalian Intestine", *Fed. Proc.*, vol. 45, pp. 2261–2267.
Steinhardt, H. J. et al., "Kinetics and Characteristics of Absorption from an Equimolar Mixture of 12 Clycyl–Dipeptides in Human Jejunum", *Gastroenterol,* vol. 90, pp. 577–582 (1986).
Sleisenger, M. H. et al., "Amino Acid Concentrations in Portal Venous Plasma During Absorption from the Small Intestine of the Guinea Pig . . . ", *Clinical Sci. Mol. Med.,* vol. 52, pp. 259–267 (1977).
Chung, Y. C. et al., "Protein Digestion and Absorption in Human Small Intestine", *Gastroenterol,* vol. 76, pp. 1415–1471 (1979).
Adibi, S. A. et al., "Peptide Absorption and Hydrolysis", *Physiol. Gastrointestinal Tract,* pp. 1073–1095 (1987).

(List continued on next page.)

*Primary Examiner*—Jeffrey E. Russel
*Attorney, Agent, or Firm*—Foley & Lardner

[57] ABSTRACT

Complex of a drug, hormone, bio-active peptide, or immunogen with the carrier molecule vitamin B12 and a method for delivering the complex to the intestine of a host vertebrate in order to deliver the complex to the circulation of the host and thereby elicit a pharmacological response to the drug, hormone, bio-active molecule or to elicit a systemic immune response to the immunogen. The invention also provides a method for the production of the complex. Further, the invention provides medicaments containing the complex.

10 Claims, No Drawings

OTHER PUBLICATIONS

Elsehans et al., "Influence of Metal Substitution on Vitamin B12 Binding . . . ", *Biochem,* vol. 23, pp. 805–808 (1984).

Gruber, P. et al., "Some Biological Issues in Oral, Controlled Drug Delivery", *Adv. Drug Delivery Rev.,* vol. 1, pp. 1–18 (1987).

Biochimica et Biophysica Acta, vol. 243, issued 1971, Olesen et al, "Nature of Vitamin B12 Binding", pp. 66–74.

Clinica Chimica Acta, vol. 95, issued 1979, Ahrenstedt et al, "The Production of Antibodies to Vitamin B-12", pp. 419–423.

ORAL DELIVERY OF BIOLOGICALLY ACTIVE SUBSTANCES BOUND TO VITAMIN B12

This application is a divisional, of application Ser. No. 08/061,343, filed May 17, 1993, now U.S. Pat. No. 5,428,023; which is a continuation of application Ser. No. 07/759,697 filed Sep. 9, 1991 now abandoned; which is a continuation of application Ser. No. 07/600,137 filed Oct. 19, 1990 now abandoned; which is a continuation of application Ser. No. 07/084,821 filed Jun. 9, 1987 now abandoned.

TECHNICAL FIELD

The present invention relates to oral delivery systems. More particularly the invention relates to enhancing the absorption of active substances by administering these substances bound to vitamin B12 (VB12) or an analogue thereof.

BACKGROUND ART

The oral route of administration is perhaps the most preferable means of delivering an antigen or pharmaceutically active agent to man. This route does however suffer from the major disadvantage that there is generally poor uptake of antigens or pharmaceutically active agents by the gastrointestinal tract and some agents may be destroyed by prolonged exposure to proteolytic enzymes. In this regard, attempts to orally immunize man or animals in the past have met with limited success. Effective vaccination has generally only been achieved by the administration of large quantities of antigen or by combining parenteral priming with oral boosting. Recent work by us utilizing a number of molecules with the ability to bind to the intestinal mucosa has demonstrated effective oral immunization using low doses of these binding proteins or by coupling various antigens or haptens to these carriers. Uptake and delivery to the circulation of these molecules from the intestine seemed to be due to receptor mediated endocytosis.

It has been known for some time that a number of specific uptake mechanisms exist in the gut for uptake of dietary molecules. Thus there are specific uptake mechanisms for monosaccharidase, disaccharides, amino acids and vitamins. Most of these uptake mechanisms depend upon the presence of a specific protein or enzyme such as monosaccharidase or disaccharidase situated in the mucosal lamina propria which binds to the molecule and transports it into the cells lining and lamina propria.

Two notable exceptions to these uptake mechanisms are found with iron transport and VB12 uptake. In both these cases a specific binding protein is released into the intestine, which binds to its ligand in the lumen of the gut.

Thus, during iron uptake in the intestine transferrin is released from the stomach, binds to iron and is in turn bound by a receptor on the duodenal mucosa. The receptor-transferrin-iron complex is then taken up by receptor mediated endocytosis.

Similarly, the absorption of physiological amounts of VB12 by the gut requires that it be complexed with a naturally occurring transport protein known as intrinsic factor (IF) (1–5). This protein is released into the lumen of the stomach by parietal cells in the fundus. Once bound to intrinsic factor, the VB12.IF complex interacts with a membrane bound receptor for IF located on the terminal ileum of the small intestine. The receptor-IF-VB12 complex is then internalized by a process of receptor mediated endocytosis (RME). Allen and Majerus (7) demonstrated that it is possible to chemically modify VB12, couple it to a resin and use the VB12-resin to affinity purify IF. This finding suggested to us that it may be possible to couple large macromolecules (such as the resin used by Allen and Majerus) to VB12 and to still preserve it's ability to interact specifically with intrinsic factor. By coupling molecules to VB12 in such a way as to preserve the ability of VB12 to interact with intrinsic factor it was hoped that we could use the natural uptake mechanism for VB12, to deliver various proteins, drugs or other pharmaceutically active molecules to the circulation.

It is thus the object of this invention to utilize the VB12 uptake mechanism to transport active substances such a drugs, hormones, antigenic material and the like, covalently coupled to VB12 or an analogue thereof, from the intestinal lumen into the circulation.

DISCLOSURE OF THE INVENTION

In a first embodiment the invention provides a complex which comprises at least one active substance linked to at least one carrier molecule which is VB12 or an analogue thereof wherein the ability of the carrier to undergo the binding reactions necessary for uptake and transport of VB12 in a vertebrate host and the activity of the active substance are substantially maintained.

In the context of the present invention, the term active substance includes all, part, an analogue, homologue, derivative or combination thereof, of a hormone, bio-active peptide, therapeutic agent, antigen or hapten.

Preferred active substances for delivery according to the invention include: hormones and bioactive peptides such as LHRH, insulin, testosterone, interferon, PMSG, HCG and inhibin; therapeutic agents such as neomycin, salbutamol, pyrimethamine, penicillin G, methicillin, carbenicillin, pethidine, xylazine, ketamine hydrochloride, mephenesin and iron dextran; antigens or haptens including allergens, proteins, polysaccharides and secretory products such as grass pollens (for instance barley and couch), weed pollens (e.g. clover, dock) tree pollens (e.g. ash, cyprus), plant pollens (e.g. broom), epithelia (e.g. cat hair, dog hair, pig hair) and house dust mite, wheat chaff and kapok; a protein derived from or immunogens against influenza, measles, Rubella, smallpox, yellow fever, diphtheria, tetanus, cholera, plague, typhus, BCG, tuberculosis causing agents, *Haemophilus influenzae, Neisseria catarrhalis, Klebsiella pneumoniae*, pneumococci, streptococci; a secretory product derived from diphtheria, tetanus, cholera, plague, typhus, tuberculosis causing agents, *Haemophilus influenzae, Neisseria catarrhalis, Klebsiella pneumoniae*, pneumococci, streptococci, *Streptococcus mutans*, or is derived from a malarial parasite or the causitive agent of coccidiosis in chickens.

Preferred analogues of VB12 include cyanocobalamin (CN-Cbl), aquocobalamin, adenosylcobalamin, methylcobalamin, hydroxycobalamin, cyanocobalamin carbanalide, and 5-o-methylbenzylcobalmin [(5-OMeBza)CN-Cbl] as well as the desdimethyl, monoethylamide and the methylamide analogues of all of the above. Also included are the various analogues and homologues of cobamamide such as coenzyme B12 and 5'-deoxyadenosylcobalamin. Other analogues include chlorocobalamin, sulfitocobalamin, nitrocobalamin, thiocyanatocobalamin, benzimidazole derivatives such as; 5,6-dichlorobenzimidazole, 5-hydroxybenzimidazole, trimethylbenzimidazole, as well as adenosylcyanocobalamin [(Ade)CN-Cbl], cobalamin lactone, cobalamin lactam and the anilide, ethylamide, monocarboxylic and dicarboxylic acid derivatives of VB12 or its analogues.

Preferred derivatives of VB12 include the mono-, di- and tricarboxylic acid derivatives or the proprionamide derivatives of VB12. Carriers may also include analogues of VB12 in which the cobalt is replaced by zinc or nickel. The corrin ring of VB12 or its analogues may also be substituted with any substituent which does not effect its binding to IF.

In a preferred embodiment of the invention there is provided a complex comprising the lys-6 form of LHRH and VB12.

The complexes of this invention, of coupled active substances can be used to deliver these substances to any uni or multicellular organism with a requirement for, and a specific transport mechanism for VB12. For example, bacteria resistant to a particular antibiotic where the resistance is mediated by the loss of ability to transport the antibiotic inside the cell, could be overcome by this procedure. A VB12-antibiotic complex could thus be effectively delivered inside the bacterial cell via the VB12 transport mechanism. This could lead to an ability to reutilize a number of antibiotics whose current use has become limited by development of bacterial resistance. Delivery of active substances, of the type described above, could be achieved to a wide variety or organisms, particularly parasites of humans or animals.

In another embodiment the invention provides a process for the production of a complex comprising, at least one active substance linked to at least one carrier molecule, said carrier molecule being VB12 or an analogue thereof, wherein the ability of the carrier to undergo the binding reactions necessary for uptake and transport of VB12 in a vertebrate host and the activity of the active substance are substantially maintained which process comprises one or more of the following steps:

a) reacting the active substance with the carrier to form said complex:

b) chemically modifying the active substance to provide at least one functional group capable of forming a chemical linkage, and reacting the active substance and carrier to form said complex;

c) chemically modifying the carrier to provide at least one functional group capable of forming a chemical linkage and reacting the active substance and carrier to form said complex;

d) chemically modifying the active substance and the carrier to provide functional groups capable of forming a chemical linkage, and reacting the active substance and carrier to form said complex;

e) reacting the active substance with at least one cross-linking agent and reacting the active substance and the carrier molecule to form said complex;

f) reacting the carrier with at least one cross-linking agent and reacting the active substance and carrier to form said complex;

g) reacting the active substance and carrier with at least one cross-linking agent and reacting the active substance and carrier to form said complex.

A preferred process of the invention comprises;

(i) preparing the mono-acid derivative of VB12 by mild acid hydrolysis, and purifying the derivative;

(ii) chemically modifying an active substance to provide at least one functional group capable of forming a chemical linkage; and (iii) reacting the modified active substance and mono-acid derivative of VB12 to form said complex.

The cross-linking agent may contain a disulfide bond or be cleavable by acid, base or periodate. Examples of cross-linking agents include N-(4-azidophenylthio)phthalimide, 4,4'-dithiobisphenylazide, dithiobis(succinimidylpropionate), dimethyl-3,3'-dithiobispropionimidate.2HCl, 3,3'-dithiobis-(sulfosuccinimidylpropionate), ethyl-4-azidophenyl-1,4-dithiobutyrimidate, HCl, N-succinimidyl-(4-azidophenyl)-1,3'-dithiopropionate, sulfosuccinimidyl-2-(m-azido-o-nitrobenzamido)-ethyl-1,3'-dithiopropionate, sulfosuccinimidyl-2-(p-azidosalicylamido)-ethyl-1,3'dithiopropionate, N-succinimidyl-3-(2-pyridyldithio)propionate, sulfosuccinimidyl-(4-azidophenyldithio)-propionate, and 2-iminothiolane. Preferred cross-linking agents are disuccinimidyl tartrate and bis-[2-(succinimidyloxycarbonyloxy)-ethyl]sulfone.

Suitably, cross-linking of the carrier and active substance may be achieved by acid hydrolysis of the amide groups of the propionamide side chains adjacent to rings A, B and C of VB12 and coupling to suitable groups of the active substance.

In a further embodiment of the invention there is provided a medicament which comprises a complex according to the invention together with a pharmaceutically acceptable carrier or diluent.

Examples of pharmaceutically acceptable carriers and diluents include typical carriers and diluents such as sodium bicarbonate solutions and similar diluents which neutralize stomach acid or have similar buffering capacity, glycols, oils, oil-in-water or water-in-oil emulsions, and include medicaments in the form of emulsions, gels, pastes and viscous colloidal dispersions. The medicament may be presented in capsule, tablet, slow release or elixir form or as a gel or paste. Furthermore, the medicament may be provided as a live stock feed or as food suitable for human consumption.

The invention also provides an antibacterial formulation comprising a complex according to the invention, in which the active substance is an antibacterial active substance together with a carrier or diluent therefor.

In another embodiment the invention provides a method of enhancing a host vertebrate's response to an orally administered active substance which method comprises the oral administration of an effective amount of said active substance as a complex according to the invention, or of a medicament according to the invention.

The invention also provides a method of selectively modulating the magnitude and/or type of immune response to an antigen or hapten, which method comprises orally administering an effective amount of said antigen or hapten as a complex according to the invention, or of a medicament according to the invention.

The invention also provides a method of delivering an active substance to any unicellular or multicellular organism, including bacteria, protozoa, or parasites, which has a requirement for VB12 as well as a specific uptake mechanism for the same, which method comprises administering a complex of the invention to the organism. In this manner bacteria which are resistant to an antibiotic due to the loss of their ability to transport the antibiotic into the cell could be once again made sensitive to the antibiotic by coupling the antibiotic to VB12 and using the natural VB12 uptake system of the bacteria to deliver the antibiotic into the cell. In this fashion a number of antibiotics whose use has been discontinued due to the occurrence of bacterial resistance could regain pharmacological significance.

In a further embodiment of the invention there is provided a method of delivering an active substance across the blood/brain barrier or across the placenta into a developing foetus by administering a complex of the invention. Delivery of such substances would occur through the natural VB12 uptake mechanisms at these barriers.

BEST MODE FOR CARRYING OUT THE INVENTION

Materials

Bovine serum albumen (BSA), VB12, p-nitrophenol, LHRH acetate salt, and neomycin sulfate were all purchased from Sigma Chemical Co. St. Louis, Mo. USA.

1-ethyl-3-(dimethylaminopropyl)carbodiimide HCl (EDAC) was obtained from BIORAD Labs, California, while N,N'dicyclohexylcarbodiimide (DCC) was purchased from Fluka.

PREPARATION 1

Monocarboxyl-Derivative of VB12

The acid derivative of VB12 can readily be prepared by hydrolysing native VB12 for 72 h in 0.4M HCl at room temperature. The reaction is stopped by passing the hydrolysate down an ion-exchange column of DOWEX AG1-X8. The flow through containing the monoacid VB12 is lyophilized and resuspended in 0.2M pyridine and adjusted to pH9.05 with 1M ammonium hydroxide. The solution is then passed down a Sephadex QAE A25 previously equilibrated with 0.2M pyridine and the monoacid eludated with a gradient from 0.4M pyridine to 0.4M, 0.16M acetic acid. The fractions containing the purified mono-acid are pooled and lyophilized.

The following examples illustrate preferred embodiments of the invention and should not be construed as limiting thereon.

The monocarboxyl VB12 can be covalently crosslinked to any amino containing compound by the use of a suitable carbodiimide.

EXAMPLE 1

VB12-BSA

VB12-BSA complex was formed by mixing an equal weight of COOH-B12 with BSA in distilled water, the pH was adjusted to 6.5 with 1M NaOH and an equal weight of solid EDAC was added to the solution and allowed to react overnight. Free, unreacted COOH-B12 was removed by chromatography of Sephadex G-25, followed by repeated ethanol precipitation of the VB12-BSA complex.

EXAMPLE 2

VB12-Lys-6-LHRH

Monocarboxyl VB12 plus 1.5 equivalents of n-hydroxysuccinamide were dissolved in cold (4° C.) dimethyl formamide (DMF). To this solution was added 1.1 equivalents of dicyclohexylcarbodiimide (DCC) in DMF. The solutions were warmed to room temperature and allowed to react for 1 hour. Lys-6-LHRH dissolved in DMF containing triethylamine was added and allowed to react overnight. The resultant complex was separated from the free reactants by chromatography on Sephadex G-25 followed by reverse phase HPLC.

EXAMPLE 3

VB12-Neomycin

The total acid hydrolisate of VB12 was adjusted to pH6.5 with NaOH, an equal weight of neomycin sulfate was added to the solution followed by an equal weight of EDAC. The conjugation was allowed to proceed overnight after which the conjugate was separated from unreacted reagents by chromatography on G-25 and reverse phase HPLC.

All reactions and purification procedures were monitored by thin layer chromatography. The degree of VB12 substitution of BSA was determined by spectrophotometric scanning of the conjugate using O.D.278 extinction values of 0.6 and 11.5, for 1 mg/ml solutions of BSA and VB12, respectively, and an O.D.361 of 20.4 for VB12.

Female C57B1/6J mice (18–22 g) were obtained from the Animal Resources Centre (Perth, Western Australia). All mice received conjugate preparations in 0.5 ml of 0.1M carbonate/bicarbonate buffer pH9.5 using a specially prepared feeding needle. Mice were fed on days 0 and 14. On day 21 the mice were bled from the orbital plexus. Antibody titres of serum were determined by ELISA using alkaline phosphatase conjugated anti-mouse serum.

EXAMPLE 4

Stimulation of serum antibodies following oral administration of VB12-BSA complex The possible potential for VB12 deliver protein molecules, covalently linked to it, from the intestine to the circulation was investigated. The immune response generated to this complex was compared to that generated by the protein fed alone or together with VB12, or to the protein injected intramuscularly.

As seen in Table 1, feeding mice with microgram quantities of BSA or FGG coupled to VB12 resulted in the stimulation of significant serum antibody responses to the BSA or FGG respectively. Feeding of either protein in similar amounts or in a 50 fold excess either mixed with VB12 or without VB12 resulted in the stimulation of no anti-BSA or anti-FGG antibodies. Feeding of these VB12-protein complexed was also capable of stimulating good cellular immunity (as measured by the footpad assay for DTH)

TABLE 1

Immune response to orally presented VB12 – BSA or VB12 – FGG complex

| Oral Immunogen | Serum Antibody Response* | Footpad Response* |
|---|---|---|
| BSA (50 μg) | <4 | 0 |
| BSA (2500 μg) | <4 | nd |
| VB12 | <4 | 0 |
| VB12 + BSA | <4 | 0 |
| VB12 – BSA | 135 ± 198 | 17.3 ± 5 |
| FGG | <4 | 0 |
| VB12 + FGG | <4 | 0 |
| VB12 – FGG | 1584 ± 647 | 23.3 ± 6 |
| FGG + FGG s.c. | 16504 ± 3047 | 27.4 ± 4 |

TABLE 1-continued

Immune response to orally presented VB12 – BSA or VB12 – FGG complex

| Oral Immunogen | Serum Antibody Response* | Footpad Response* |
|---|---|---|

*The reciprocal on the antiserum dilution that gave an ELISA reading of 0.5 after 45 min. at 37° C. on day 21 after initial feeding. Each value represents the mean of 15 mice ±1 standard deviation. Mice received two feedings of antigen (50 μg) on days 1 and 14. On day 21 mice were bled from the retro orbital plaxus and the antibody titres measured by ELISA as described previously (Russell-Jones et al., 1984). Each protein molecule was substituted with an average of 5 VB12 groups.
+ Footpad swelling was measured in mm using a microcaliper. All groups received a 50 μg priming dose of antigen followed by challenge with 10 μg of the immunizing antigen in the right foot and 10 μg of ovalbumen in the left footpad. Swelling was measured after 24 h.

EXAMPLE 5

Oral delivery of VB12-LHRH as a means of stimulating ovulation

Although a number of hormones as oestrogen and progesterone are actively absorbed upon oral administration, there are may other which have little effect when given per os. Noteable amongst these hormones is the peptide hormone lutenizing hormone releasing hormone (LHRH), or gonadotrophin releasing hormone (GnRH). This hormone is normally secreted by the anterior pituitary and is responsible for the control of release of lutenizing hormone (LH) and follicle stimulating hormone (FSH). Parenteral injections of LHRH have previously been shown to be effective in stimulating FSH and LH release, however orally presented LHRH has little effect. Many studies have been performed on varying the sequence of LHRH, with the result that a number of agonists and antagonists have now been identified. Perhaps one of the most powerful agonists identified to date is the D-Lys-6 analogue of LHRH (D-Lys-6.LHRH). As the epsilon amino group on the lysine of this analogue is readily accessible for peptide cross-linking it was decided to use the DCC method to link monocarboxyl VB12 to D-Lys6.LHRH and to test it's efficacy upon oral administration.

The D-lys-6 analogue of LHRH was synthesized by us and purified by reverse phase HPLC. The purified analogue was coupled to monocarboxyl VB12 using DCC as described in Example 2. The conjugated product was purified by Sephadex G-25 chromatography in 10% acetic acid, followed by HPLC Chromatography.

Mature C57B1/6J female mice were treated in the following fashion:—On day O all mice received a subcutaneous (s/c) superovulating dose of pregnant mare serum gonadotraphin (PMSG) to stimulate the growth of ovarian follicles. After 48 hours mice received various doses of LHRH, Lys-6-LHRH or saline. On day 3 mice were sacrificed and examined for ovulation. Ovulation was assessed by examining for the presence of corpora haemorrhagica on the ovaries using a stereoscopic microscope at 80X power.

The results below show that by coupling Lys-6-LRH to VB12 it is possible to deliver the analogue orally and to still observe a biological effect as exemplified by it's ability to stimulate ovulation in developing follicles. The inability of this preparation to exert it's effect when injected intravenously presumably reflects the rapid clearance of free VB12 when it is not complexed to transcobalamin II.

TABLE 2

Demonstration of the biological activity of Lys-6-LHRH

| Treatment | | | Number of mice |
|---|---|---|---|
| Day 0 | Day 2 | | ovulating |
| PMSG 8IU | Lys-6-LHRH | 50 μg iv | 3/4 |
| PMSG 8IU | LHRH | 50 μg iv | 1/4 |
| PMSG 8IU | Saline | 250 μg iv | 0/4 |
| PMSG 4IU | Lys-6-LHRH | 50 μg iv | 3/3 |
| PMSG 4IU | LHRH | 50 μg iv | 1/3 |
| PMSG 4IU | Saline | 250 μl iv | 0/3 |

TABLE 3

Demonstration of the ability of VB12 to deliver the Lys-6-LRH orally

| Treatment | | | Number of mice |
|---|---|---|---|
| Day 0 | Day 2 | | ovulating |
| PMSG 8IU | VB12-Lys-6-LHRH | 50 μg iv | 0/5 |
| PMSG 8IU | VB12-Lys-6-LHRH | 50 μg/os | 3/5 |
| PMSG 8IU | LHRH | 50 μg/os | 1/5 |
| PMSG 8IU | Saline | 250 μl/os | 0/5 |

TABLE 4

Dose response to orally presented VB12-Lys-6-LHRH

| Treatment | | | Number of mice |
|---|---|---|---|
| Day 0 | Day 2 | | ovulating |
| PMSG 8IU | VB12-Lys-6-LHRH | 50 μg/os | 4/5 |
| PMSG 8IU | VB12-Lys-6-LHRH | 25 μg/os | 3/5 |
| PMSG 8IU | VB12-Lys-6-LHRH | 12 μg/os | 5/5 |
| PMSG 8IU | VB12-Lys-6-LHRH | 6 μg/os | 2/5 |
| PMSG 8IU | LHRH | 50 μg/os | 1/5 |
| PMSG 8IU | LHRH | 25 μg/os | 1/5 |
| PMSG 8IU | LHRH | 12 μg/os | 0/5 |
| PMSG 8IU | LHRH | 5 μg/os | 0/5 |
| PMSG 8IU | HCG | 10IU iv | 5/5 |
| PMSG 8IU | Saline | 250 μg/os | 0/5 |

EXAMPLE 6

A number of drugs including the antibiotic, neomycin, are highly effective antibiotics when injected parenterally, however they are completely ineffective when given orally as they cannot be transported across the intestinal epithelium. It was therefore decided to see if VB12 could act as a carrier for an antibiotic (neomycin) which normally has no effect upon a systemic infection when the antibiotic was given orally.

Neomycin was covalently linked to VB12 as described in Example 3 and fed to mice infected with *S. typhimurium*.

Oral administration of neomycin, or neomycin plus VB12 was not able to eliminate systemic infection with *S. typhimurium*. When neomycin was coupled to VB12, however, a significant quantity of the conjugate was transported across the intestinal epithelium and was capable of eliminating a systemic Salmonella infection. Table 3 shows that mice infected with *S. typhimurium* could be saved by either feeding VB12.neomycin conjugate (1 mg total dose) or by the i.m. injection of neomycin or VB12.neomycin (both 1 mg total dose). All other treatments failed to prevent death due to infection. In addition, the extent to which orally presented VB12.neomycin was capable of clearing infective particles from the liver and spleen of experimental animals suggests that, at least for this dosage, VB12.neomycin is comparable to an i.m. injection of neomycin alone or the neomycin.VB12 conjugate (Table 5).

TABLE 5

Bactericidal properties of VB12-neomycin conjugates

| Treatment | Route | Survivors (day 10) | |
|---|---|---|---|
| | | Number | Percentage |
| Saline | oral | 0 | 0 |
| Neomycin | oral | 0 | 0 |
| VB12 | oral | 0 | 0 |
| Neomycin + VB12 | oral | 0 | 0 |
| Neomycin − VB12 | oral | 2 | 100 |
| Saline | i.m. | 0 | 0 |
| Neomycin | i.m. | 2 | 100 |
| Neomycin − VB12 | i.m. | 2 | 100 |

Male-C57B1/6J mice (/group) were fed $1\times10^6$ S. typhimurium on day 0. On day 3 mice received either saline, VB12, VB12+neomycin (Neomycin+VB12), VB12 coupled to neomycin (Neomycin−VB12), or neomycin alone. A total dose of 1 mg was administered as five smaller doses each separated by 12 hours. Neomycin was coupled to VB12 and the conjugate purified as outlined in Example 3.

It is possible to covalently couple VB12 to proteins (FGG and BSA), hormones (LHRH) and antibiotics (neomycin) and to utilize the natural active uptake mechanism for VB12 to transport these molecules from the lumen of the gut into the systemic circulation while retaining full immunogenicity and/or biological activity of the molecules coupled to VB12. The importance of these findings lie in the potential use of VB12 as a specific carrier of highly potent hormones, antibiotics and vasoactive peptides which currently must be repeatedly administered by injection at considerable costs and inconvenience.

INDUSTRIAL APPLICABILITY

The present invention provides a simple and novel technique for the specific oral presentation of various molecules previously incapable of being transported across the gut in significant amounts or in producing a significant systemic immune response upon oral feeding of various antigens. These antigens would not normally elicit an immune response when fed unless very large quantities of antigen were administered. Similarly various active molecules which are normally only poorly absorbed from the intestine can be covalently linked to VB12 and so render them susceptable to intestinal uptake.

REFERENCES

1. Castle, W. B. N. Engl. J. Med, 24, 603–611 (1953)
2. Fox, H. J., Castle, W. B. Am. J. Med. Sci., 203, 18–26
3. Hoedemaeker, P. J., Ables J., Wachters, J. J., Averds, A., Nieweg, H. O., Lab. Invest., 15, 1163–1169 (1966)
4. Allen, R. H. Majerus, P. W. J. Biol. Chem.,; 247, 7702–7708 (1972)
5. Allen, R. H. Majerus, P. W. J. Biol. Chem.,; 247, 7709–7717 (1972)
6. Grasbech, R. Progr. Haematol. 6, 233–260 (1969)
7. Allen, R. H. Majerus, P. W. J. Biol. Chem.,; 247, 7695–7701 (1972)
8. Russel-Jones, G. J., Gotschlich, E. C. Blake, M. S. J. Exp. Med., 160, 1476- (1984)
9. Sedgwick, J. D. Holt, P. G. J. Immunol. Meth., 87 37–44 (1986)

We claim:

1. An orally administrable complex comprising an antigen or hapten that is covalently linked via a cross-linking agent to a vitamin B12 carrier molecule, wherein
   (A) said carrier molecule is capable of binding in vivo to intrinsic factor, thereby enabling uptake and transport of the complex from the intestinal lumen of a vertebrate host via intrinsic factor to the systemic circulation of said host, and
   (B) said cross-linking agent links said antigen or hapten to a carboxyl group of an acid-hydrolyzed propionamide side chain adjacent to ring A, ring B or ring C of said carrier molecule, and
   said antigen or hapten is an allergen, protein, polysaccharide or secretory product selected from the group consisting of polysaccharides, grass pollen, weed pollen, tree pollen, plant pollen, cat hair, dog hair, pig hair, other epithelia, house dust mite, wheat chaff, kapok, a protein from or immunogens against influenza, measles, Rubella, smallpox, yellow fever, diphtheria, tetanus, cholera, plague, typhus, BCG, tuberculosis causing agents, *Haemophilus influenzae, Neisseria catarrhalis, Klebsiella pneumoniae*, pneumococci, streptococci, a malarial parasite or the causative agent of coccidiosis in chickens, a secretory product from diphtheria, tetanus, cholera, plague, typhus, tuberculosis causing agents, *Haemophilus influenzae, Neisseria catarrhalis, Klebsiella pneumoniae*, pneumococci, streptococci, and *Streptococcus mutans*.

2. A complex according to claim 1, wherein said vitamin B12 carrier molecule is selected from the group consisting of cyanocobalamin, aquocobalamin, adenosylcobalamin, methylcobalamin, hydroxycobalamin, cyanocobalamin carbanilide, 5-0-methylbenzylcobalamin, desdimethyl, monoethylamide and methylamide analogues of cyanocobalamin, aquocobalamin, adenosylcobalamin, methylcobalamin, hydroxycobalamin, cyanocobalamin carbanilide and 5-0-methylbenzylcobalamin, coenzyme B12, 5'-deoxyadenosylcobalamin, chlorocobalamin, sulphitocobalamin, nitrocobalamin, thiocyanatocobalamin, adenosylcyanocobalamin, cobalamin lactone, cobalamin lactam, vitamin B12 anilide, vitamin B12 propionamide, and a vitamin B12 molecule in which one or two corrin ring side chains are free carboxylic acids.

3. A complex according to claim 1, wherein said vitamin B12 carrier molecule includes a central metal atom selected from the group consisting of Ni and Zn.

4. A complex according to claim 1, wherein said cross-linking agent is selected from the group consisting of N-(4-azidophenylthio)phthalimide, 4,4'-dithiobis-phenylazide, dithiobis(succinimidylpropionate), dimethyl-3,3'-dithiobispropionimidate.2HCl, 3,3'-dithiobis(sulphosuccinimidyl-propionate), ethyl-4-azidophenyl-1,4-dithiobutyrimidate.HCl, N-succinimidyl-(4-azidophenyl)-1,3'-dithiopropionate, sulphosuccinimidyl-2-(m-azido-o-nitrobenzamido)-ethyl-1,3'-dithiopropionate, sulphosuccinimidyl-2-(p-azidosalicylamido)-ethyl-1,3'-dithiopropionate, N-succinimidyl-3-(2-pyridyldithio)propionate, sulphosuccinimidyl-(4-azidophenyldithio)-propionate and 2-iminothiolane.

5. A complex according to claim 1, wherein said cross-linking agent is bis(2-(succinimidyloxycarbonyloxy) ethyl) sulphone.

6. A formulation comprising (i) a complex according to claim 1 and (ii) an orally and pharmaceutically acceptable carrier or diluent.

7. A formulation according to claim 6, wherein said formulation is in an oral delivery form selected from the group consisting of a capsule, a tablet, an emulsion, a viscous colloidal dispersion, an elixir, a gel and a paste.

8. A method of treating a patient with an antigen or hapten, comprising the steps of
  (1) providing an orally administrable complex comprising said antigen or hapten covalently linked via a cross-linking agent to a vitamin B12 carrier molecule, wherein
    (A) said carrier molecule is capable of binding in vivo to intrinsic factor, thereby enabling uptake and transport of the complex from the intestinal lumen of said patient via intrinsic factor to the systemic circulation of said patient, and
    (B) said cross-linking agent links said antigen or hapten to a carboxyl group of an acid-hydrolyzed propionamide side chain adjacent to ring A, ring B or ring C of said carrier molecule;
  and
  (2) orally administering said complex to said patient so as to elicit a physiological effect associated with the presence of said antigen or hapten in the systemic circulation of said patient.

9. A complex according to claim 1, wherein said vitamin B12 carrier molecule is a cyanocobalamin methylamide or a cobalamin ethylamide.

10. A complex according to claim 1, wherein said vitamin B12 carrier molecule is selected from the group consisting of 5,6-dichlorobenzimidazolecobalamin, 5-hydroxybenzimidazole-cobalamin, and trimethylbenzimidazolecobalamin.

* * * * *